United States Patent

Hargreaves

[11] Patent Number: 5,830,854
[45] Date of Patent: Nov. 3, 1998

[54] METHOD OF TREATING CYSTIC FIBROSIS USING A TACHYKININ RECEPTOR ANTAGONIST

[75] Inventor: Richard John Hargreaves, Harlow, United Kingdom

[73] Assignee: Merck Sharp & Dohme, Limited, Hoddesdon, England

[21] Appl. No.: 496,118

[22] Filed: Jun. 27, 1995

Related U.S. Application Data

[63] Continuation of Ser. No. 166,437, Dec. 14, 1993, abandoned.

[30] Foreign Application Priority Data

Dec. 14, 1992 [GB] United Kingdom .................... 9226047
Dec. 14, 1992 [GB] United Kingdom .................... 9226056

[51] Int. Cl.⁶ .......................... A61K 38/00; A61K 31/44; A01N 34/18; A01N 43/40
[52] U.S. Cl. ..................... 514/9; 514/2; 514/14; 514/15; 514/354; 514/355; 514/415; 514/210; 514/352; 514/396; 514/364; 514/430; 514/431; 514/432; 514/444; 514/449; 514/451; 514/461; 514/475; 514/481; 514/485; 530/327; 530/328
[58] Field of Search .............................. 514/2, 9, 14, 15, 514/354, 355, 415, 210, 352, 396, 364, 430, 431, 432, 444, 449, 451, 461, 475, 481, 485; 530/327, 328

[56] References Cited

U.S. PATENT DOCUMENTS

| | | | |
|---|---|---|---|
| 4,866,072 | 9/1989 | Edwards et al. | 514/291 |
| 5,100,647 | 3/1992 | Agus et al. | 514/286 |
| 5,162,348 | 11/1992 | Glass et al. | 514/359 |
| 5,242,930 | 9/1993 | Baker et al. | 514/305 |
| 5,262,178 | 11/1993 | Camine et al. | 424/94.67 |
| 5,273,986 | 12/1993 | Holland et al. | 514/365 |
| 5,328,927 | 7/1994 | Lewis et al. | 514/415 |

FOREIGN PATENT DOCUMENTS

| | | |
|---|---|---|
| 0 327 009 | 8/1989 | European Pat. Off. . |
| 0 336 230 | 10/1989 | European Pat. Off. . |
| 0 353 732 | 2/1990 | European Pat. Off. . |
| 0 360 390 | 3/1990 | European Pat. Off. . |
| 0 385 043 | 9/1990 | European Pat. Off. . |
| 0 394 989 | 10/1990 | European Pat. Off. . |
| 0 429 366 A1 | 5/1991 | European Pat. Off. . |
| 0 430 771 A1 | 6/1991 | European Pat. Off. . |
| 0 436 334 A2 | 7/1991 | European Pat. Off. . |
| 0 499 313 A1 | 8/1992 | European Pat. Off. . |
| 0 428 434 A2 | 5/1991 | France . |
| 2 216 529 | of 0000 | United Kingdom . |
| 90/05729 | 5/1990 | WIPO . |
| 91/18899 | 12/1991 | WIPO . |
| 92/01688 | 2/1992 | WIPO . |
| 92/06079 | 4/1992 | WIPO . |
| 92/15585 | 9/1992 | WIPO . |

OTHER PUBLICATIONS

British J. Pharmacol. (1994), vol. 113, pp. 1183–1190, "Sensory–efferent Neural Control of Mucus Secretion . . . " by S. I. Ramnarine et al.

British J. Pharmacol. (1992), vol. 107, pp. 685–789, "Pharmacological profile of a high affinity dipeptide NK1 receptor antagonist, FK888" by T. Fujii et al.

Regulatory Peptides, (1988), vol. 22, 127, "Pharmacological Specificity of Synthetic Peptides as Antagonists at Tachykinin Receptors" by A.T. McKnight et al.

Chung, K. Fan, Effects of nedocromil sodium on airway neurogenic mechanisms, J. Allergy Clin. Immunol., 98 (5, Pt. 2), pp. S112–S117, 1996.

Javdan, et al., Nedocromil sodium reduces allergen–induced plasma extravasation . . . , Allergy (Copenhagen), vol. 50, No. 10, pp. 825–829, 1995.

Sekizawa, et al., Enkephalinase inhibitor potentiates mammalian tachykinin–induced contraction . . . , J. Pharmacol. Exp. Ther., vol. 243, No. 3, pp. 1211–1217, 1987.

*Primary Examiner*—Cecilia J. Tsang
*Assistant Examiner*—Jennifer Harle
*Attorney, Agent, or Firm*—J. Eric Thies; David L. Rose

[57] ABSTRACT

Tachykinin receptor antagonists are useful for the treatment of cystic fibrosis.

11 Claims, No Drawings

METHOD OF TREATING CYSTIC FIBROSIS USING A TACHYKININ RECEPTOR ANTAGONIST

This is a continuation of application Ser. No. 08/166,437 filed Dec. 14, 1993, now abandoned.

This invention relates to tachykinin receptor antagonists for use in the treatment of cystic fibrosis.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P: Arg-Pro-Lys-Pro-Gln-Gln-Phe-Phe-Gly-Leu-Met-$NH_2$

Neurokinin A: His-Lys-Thr-Asp-Ser-Phe-Val-Gly-Leu-Met-$NH_2$

Neurokinin B: Asp-Met-His-Asp-Phe-Phe-Val-Gly-Leu-Met-$NH_2$

Tachykinin receptor antagonists and in particular NK-1 receptor antagonists have been referred to in ceonnection with chronic obstructive airway diseases (EP-A-436334), asthma (WO 92/06079) and bronchopneumonia and bronchospasm (EP-A-92200303.3) Tachykinins such as substance P have been implicated in the control of mucous secretion (S. Meini et al., and Kno H. P. et al., 1992, Int Conference of the American Lung Association and the American Thoracic Society, Am. Rev. Respir. Dis. 145 (4 Part 2), 1992, A370 and A369), for example in relation to cigarette smoking (Lei-Y-H et al., Am. Rev. Respir. Dis 45 (4 Part 2), 1992, A262.

It is now suggested for the first time that a disease resulting from a genetic disfunction can be treated using a tachykinin antagonist.

Cystic fibrosis is an autosomal recessive disorder characterised by a decreased pancreatic exocrine function. It is the most common lethal condition in Caucasian children, with a heterozygote frequency of 1 in 40. The worst effects of the disorder are seen in the bronchial tree, where the infected, viscid secretions cannot be eliminated.

The present invention provides the use of a tachykinin receptor antagonist and in particular a NK1 receptor antagonist for the manufacture of a medicament for the treatment of cystic fibrosis.

In a further aspect, the present invention provides a method of treatment of cystic fibrosis which method comprises administering to a patient in need thereof a pharmacologically effective amount of a tachykinin receptor antagonist and in particular a NK1 receptor antagonist.

The patient will be a human.

Suitable compounds of use in the present invention include those disclosed in European patent applications nos. 0 353 732, 0 327 009, 0 336 230, 0 394 989, 0 360 390, 0 436 334, 0 429 366, 0 430 771, 0 499 313, 0 428 434 and 0 385 043, PCT patent applications nos. 92/01688, 92/06079, 92/15585, 91/18899 and 90/05729, and British patent no. 2216529, the contents of which applications and patent are incorporated herein by reference.

Also suitable for use in the present invention are compounds of the following general formulae (1)–(8), and pharmaceutically acceptable salts and prodrugs thereof:

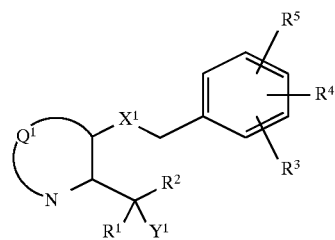

(1)

wherein $Q^1$ is the residue of an optionally substituted azabicyclic ring system;

$X^1$ represents O or S;

$Y^1$ represents H or hydroxy;

$R^1$ represents phenyl or thienyl, either of which groups may be optionally substituted by halo, trifluoromethyl or $C_{1-3}$ alkoxy, or $C_{5-7}$ cycloalkyl;

$R^2$ represents benzyl which may be substituted in the benzyl ring by halo, trifluoromethyl or $C_{1-3}$alkoxy, or $C_{5-7}$ cycloalkyl; and $R^3$, $R^4$ and $R^5$ independently represent H, $C_{1-6}$ alkyl, $C_{2-6}$ alkenyl, $C_{2-6}$ alkynyl, halo, cyano, nitro, trifluoromethyl, trimethylsilyl, —$OR^a$, $SCH_3$, $SOCH_3$, $SO_2CH_3$, —$NR^aR^b$, —$NR^aCOR^b$, —$NR^aCO_2R^b$, —$CO_2R^a$ or —$CONR^aR^b$; and $R^a$ and $R^b$ independently represent H, $C_{1-6}$ alkyl, phenyl or trifluoromethyl.

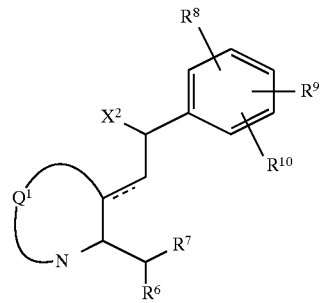

(2)

wherein $Q^1$ is as defined for formula (1) above;

the dotted line represents an optional double bond;

$X^2$ represents H, —OH, =O or halo;

$R^6$ represents H, phenyl or thienyl, which phenyl or thienyl groups may be optionally substituted by halo or trifluoromethyl;

$R^7$ represents phenyl, thienyl or benzyl, any of which groups may be optionally substituted by halo or trifluoromethyl; and $R^8$, $R^9$ and $R^{10}$ independently represent H, $C_{1-6}$ alkyl, $C_{2-6}$ alkenyl, $C_{2-6}$ alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$ or —$CONR^aR^b$; where $R^a$ and $R^b$ are as defined for formula (1) above.

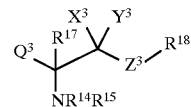

(3)

wherein $Q^3$ represents $R^{11}CR^{12}R^{13}$ or $CH_2R^{11}CR^{12}R^{13}$ where $R^{11}$ is H or hydroxy and $R^{12}$ and $R^{13}$ each independently represent optionally substituted phenyl, optionally substituted benzyl, $C_{5-7}$cycloalkyl or ($C_{5-7}$cycloalkyl)methyl;

$R^{14}$ and $R^{15}$ independently represent H; $C_{1-6}$ alkyl optionally substituted by hydroxy, cyano, $COR^c$, $COOR^c$, $CONR^cR^d$, $COC1$-$6$alkyl$NR^cR^d$, $CONR^{16}C_{1-6}$alkyl$OR^c$, $CONR^{16}C_{1-6}$alkyl$CONR^cR^d$ or $NR^cR^d$ (where $R^c$ and $R^d$ each independently represent H, $C_{1-6}$ alkyl, phenyl (optionally substituted by one or more of $C_{1-6}$alkyl, $C_{1-6}$alkoxy, halo and trifluoromethyl), phenyl($C_{1-4}$alkyl) (optionally substituted in the phenyl ring by one or more of $C_{1-6}$ alkyl, $C_{1-6}$ alkoxy, halo and trifluoromethyl) or $R^c$ and $R^d$ together form a chain $(CH_2)_p$ optionally substituted by oxo where p is 4 or 5 and where one methylene group may optionally be replaced by an oxygen atom or a group $NR^x$, where $R^x$ is H or $C_{1-6}$ alkyl, and $R^{16}$ represents H, $C_{1-6}$alkyl, phenyl (optionally substituted by one or more of $C_{1-6}$alkyl, $C_{1-6}$alkoxy, halo and trifluoromethyl) or phenyl($C_{1-4}$alkyl) (optionally substituted in the phenyl ring by one or more of $C_{1-6}$alkyl, $C_{1-6}$alkoxy, halo and trifluoromethyl); phenyl ($C_{1-4}$ alkyl) (optionally substituted by one or more of $C_{1-6}$ alkyl, $C_{1-6}$ alkoxy, halo and trifluoromethyl in the phenyl ring); $C_{2-6}$ alkenyl; $C_{2-6}$ alkynyl; $COR^c$; $COOR^c$; $COC_{1-6}$alkylhalo; $COC_{1-6}$alkyl$NR^cR^d$; $CONR^{16}C_{1-6}$alkyl$CONR^cR^d$; $CONR^cR^d$; or $SO_2R^c$; (where $R^c$, $R^d$ and $R^{16}$ are as previously defined) or $R^{14}$ and $R^{15}$ together form a chain $(CH_2)_q$ optionally substituted by oxo where q is 4 or 5 and where one methylene group may optionally be replaced by an oxygen atom or a group $NR^x$, where $R^x$ is H or $C_{1-6}$ alkyl;

$R^{17}$ represents H, $C_{1-6}$ alkyl or $C_{2-6}$alkenyl;

$R^{18}$ represents $C_{1-3}$ alkyl substituted by a phenyl group which may itself optionally be substituted by one or more of $C_{1-6}$ alkyl, $C_{2-6}$ alkenyl, $C_{2-6}$ alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ and $CONR^aR^b$, where $R^a$ and $R^b$ are as defined for formula (1) above;

$X^3$ and $Y^3$ each represent H, or $X^3$ and $Y^3$ together represent a group =O; and $Z^3$ represents O, S, or $NR^{19}$, where $R^{19}$ represents H or $C_{1-6}$ alkyl.

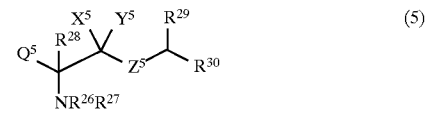 (4)

wherein $Q^4$ represents optionally substituted phenyl, optionally substituted naphthyl, optionally substituted indolyl, optionally substituted benzthiophenyl, optionally substituted benzofuranyl, optionally substituted benzyl or optionally substituted indazolyl;

$Z^4$ represents O, S or $NR^{20}$, where $R^{20}$ is H or $C_{1-6}$alkyl;

$X^4$ and $Y^4$ each represent H or $X^4$ and $Y^4$ together form a group =O;

$R^{21}$ and $R^{22}$ each independently represent H; $C_{1-6}$alkyl, optionally substituted by hydroxy, cyano, $COR^g$, $CO_2R^g$, $CONR^gR^h$, or $NR^gR^h$ (where $R^g$ and $R^h$ each independently represent H, $C_{1-12}$alkyl or phenyl optionally substituted by one or more of $C_{1-6}$alkyl, $C_{1-6}$alkoxy, halo or trifluoromethyl); phenyl($C_{1-4}$alkyl) (optionally substituted in the phenyl ring by one or more of $C_{1-6}$alkyl, $C_{1-6}$alkoxy, halo and trifluoromethyl); $COR^g$; $CO_2R^g$; $CONR^gR^h$; $CONR^g$-$COOR^h$; or $SO_2R^g$, where $R^g$ and $R^h$ are as above defined;

$R^{23}$ represents H or $C_{1-6}$alkyl; and $R^{24}$ represents H, $C_{1-6}$alkyl or phenyl (optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ and $CONR^aR^b$, where $R^a$ and $R^b$ are as defined for formula (1) above; and $R^{25}$ represents phenyl (optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ and $CONR^aR^b$, where $R^a$ and $R^b$ independently are as above defined.

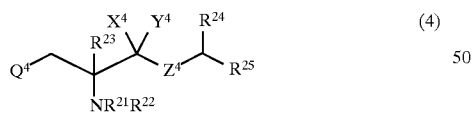 (5)

wherein $Q^5$ represents optionally substituted phenyl, optionally substituted heteroaryl or optionally substituted naphthyl;

$X^5$ and $Y^5$ each represent H, $C_{1-6}$alkyl, $C_{2-6}$alkenyl or $X^5$ and $Y^5$ together form a group =O;

$Z^5$ represents O or S;

$R^{26}$ represents H; $C_{1-6}$ alkyl optionally substituted by hydroxy, cyano, $COR^j$, $COOR^j$, $CONR^jR^k$, $COC_{1-4}$alkyl$NR^jR^k$, $CONR^jC_{1-4}$alkyl$CONR^jR^k$ or $NR^jR^k$, (where $R^j$ and $R^k$ each independently represent H, $C_{1-6}$ alkyl, phenyl optionally substituted by one or more of $C_{1-6}$alkyl, $C_{1-6}$alkoxy, halo or trifluoromethyl or phenyl ($C_{1-4}$alkyl) optionally substituted in the phenyl ring by one or more of $C_{1-6}$ alkyl, $C_{1-6}$ alkoxy, halo or trifluoromethyl); phenyl($C_{1-4}$ alkyl) (optionally substituted in the phenyl ring by one or more of $C_{1-6}$ alkyl, $C_{1-6}$ alkoxy, halo or trifluoromethyl); $C_{2-6}$ alkylene; $COR^j$; $COOR^j$; $CONHR^j$; $COC_{1-6}$alkylhalo; $COC_{1-6}$alkyl$NR^jR^k$; or $CONR^jC_{1-6}$alkyl$CONR^jR^k$, where $R^j$ and $R^k$ are as previously defined;

$R^{27}$ represents $C_{1-6}$ alkyl substituted by hydroxy, cyano, $COR^j$, $COOR^j$, $CONR^jR^k$, $COC_{1-4}$alkyl$NR^jR^k$, $CONR^jC_{1-4}$alkyl$CONR^jR^k$ or $NR^jR^k$, (where $R^j$ and $R^k$ are as above defined); phenyl($C_{1-4}$ alkyl) (optionally substituted by one or more of $C_{1-6}$ alkyl, $C_{1-6}$ alkoxy, halo and trifluoromethyl in the phenyl ring); $C_{2-6}$ alkylene; $COR^j$; $COOR^j$; $CONHR^j$; $COC_{1-6}$alkylhalo; $COC_{1-6}$alkyl$NR^jR^k$; or $CONR^jC_{1-6}$alkyl$CONR^jR^k$, where $R^j$ and $R^k$ are as previously defined;

or $R^{26}$ and $R^{27}$ together form a chain $(CH_2)_p$ optionally substituted by oxo; where p is 4 or 5 and where one methylene group may optionally be replaced by an oxygen atom or a group $NR^x$, where $R^x$ is H or $C_{1-6}$ alkyl;

$R^{28}$ represents H or $C_{1-6}$alkyl;

$R^{29}$ represents H, $C_{1-6}$ alkyl or phenyl (optionally substituted by one or more of $C_{1-6}$ alkyl, $C_{2-6}$ alkenyl, $C_{2-6}$ alkynyl, halo, cyano, nitro, trifluoromethyl, trimethylsilyl, $SR^a$, $SOR^a$, $SO_2R^a$, $OR^a$, $NR^aR^d$, $NR^aCOR^b$, $NR^aCOOR^b$, $COOR^a$ or $CONR^aR^b$, where $R^a$ and $R^b$ are as defined for formula (1) above; and $R^{30}$ represents $(CH_2)_q$phenyl, wherein q is 0, 1, 2 or 3, which may optionally be substituted in the phenyl ring by one or more of $C_{1-6}$ alkyl, $C_{2-6}$ alkenyl, $C_{2-6}$ alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ are as above defined.

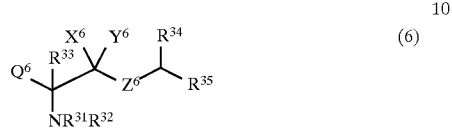

(6)

wherein $Q^6$ represents a group

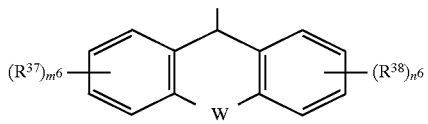

where W represents a bond, O, S, —$CH_2CH_2$—, —CH=CH— or a group $NR^{36}$, where $R^{36}$ is H or $C_{1-6}$alkyl and one or both of the phenyl rings may be replaced by a heteroaryl moiety;

$X^6$ and $Y^6$ each represent H or $X^6$ and $Y^6$ together form a group =O;

$Z^6$ represents O, S or $NR^{38}$, where $R^{38}$ represents H or $C_{1-6}$alkyl;

$R^{31}$ and $R^{32}$ independently represent H; $C_{1-6}$ alkyl optionally substituted by hydroxy, cyano, $COR^e$, $COOR^e$, $CONR^eR^f$, $COC_{1-4}$alkyl$NR^eR^f$, $CONR^eC_{1-4}$alkyl $CONR^eR^f$ or $NR^eR^f$, (where $R^e$ and $R^f$ each independently represent H, $C_{1-6}$ alkyl, phenyl (optionally substituted by one or more of $C_{1-6}$alkyl, $C_{1-6}$alkoxy, halo and trifluoromethyl) or phenyl($C_{1-4}$alkyl) (optionally substituted in the phenyl ring by one or more of $C_{1-6}$ alkyl, $C_{1-6}$ alkoxy, halo and trifluoromethyl)); phenyl ($C_{1-4}$ alkyl), (optionally substituted by one or more of $C_{1-6}$ alkyl, $C_{1-6}$ alkoxy, halo and trifluoromethyl in the phenyl ring); $C_{2-6}$ alkylene; $COC_{1-6}$alkylhalo; $COR^e$; $COOR^e$; $CONHR^e$; $COC_{1-4}$alkyl$NR^eR^f$; or $CONR^eC_{1-4}$ alkyl$CONR^eR^f$; (where $R^e$ and $R^f$ are as previously defined) or $R^{31}$ and $R^{32}$ together form a chain $(CH_2)_p$ where p is 4 or 5 and where one non-terminal methylene group may optionally be replaced by an oxygen atom or a group $NR^x$, where $R^x$ is H or $C_{1-6}$ alkyl;

$R^{33}$ represents H or $C_{1-6}$alkyl;

$R^{34}$ represents H, $C_{1-6}$ alkyl or phenyl (optionally substituted by one or more of $C_{1-6}$ alkyl, $C_{2-6}$ alkenyl, $C_{2-6}$ alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ are as defined for formula (1) above;

$R^{35}$ represents $(CH_2)_q$phenyl, wherein q is 0, 1, 2 or 3 which may optionally be substituted in the phenyl ring by one or more of $C_{1-6}$ alkyl, $C_{2-6}$ alkenyl, $C_{2-6}$ alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ are as above defined;

each $R^{37}$ and $R^{38}$ independently represents $C_{1-6}$ alkyl, $C_{2-6}$ alkenyl, $C_{2-6}$ alkynyl, halo, cyano, nitro, trifluoromethyl, trimethylsilyl, $SR^a$, $SOR^a$, $SO_2R^a$ $OR^a$, $NR^aR^b$, $NR^aCOR^b$, $NR^aCOOR^b$, $COOR^a$ or $CONR^aR^b$, where $R^a$ and $R^b$ are as above defined; and $m^6$ and $n^6$ independently represent 0, 1, 2, 3 or 4.

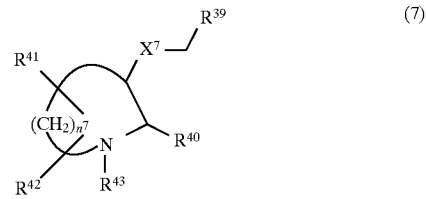

(7)

wherein $n^7$ is 1, 2 or 3 and any carbon atom of $(CH_2)_{n^7}$ may be substituted by $R^{41}$ and/or $R^{42}$;

$X^7$ represents O or S;

$R^{39}$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$ or —$CONR^aR^b$;

$R^{40}$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;

$R^{41}$ and $R^{42}$ each independently represent H, halo, $CH_2OR^{44}$, $C_{1-6}$alkyl, oxo, $CO_2R^{45}$ or $CONR^{45}R^{46}$;

$R^{43}$ represents H, $COR^{44}$, $CO_2R^{45}$, $COCONR^{45}R^{46}$, $COCO_2R^{45}$ or $C_{1-6}$alkyl optionally substituted by a group selected from ($CO_2R^{45}$, $CONR^{45}R^{46}$, hydroxy, cyano, $COR^{44}$, $NR^{45}R^{46}$, $C(NOH)NR^{45}R^{46}$, $CONHphenyl(C_{1-4}alkyl)$, $COCO_2R^{45}$ $COCONR^{45}R^{46}$ and phenyl optionally substituted by one or more substituents selected from $C_{1-6}$alkyl, $C_{1-6}$alkoxy, halo and trifluoromethyl);

$R^a$ and $R^b$ are as defined for formula (1) above;

$R^{44}$ represents H, $C_{1-6}$alkyl or phenyl; and $R^{45}$ and $R^{46}$ each independently represent H or $C_{1-6}$alkyl.

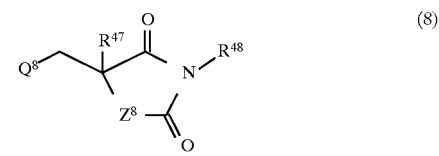

(8)

wherein $Q^8$ represents a phenyl group substituted by one or more halo, optionally substituted naphthyl, optionally substituted indolyl, optionally substituted benzthiophenyl, optionally substituted benzofuranyl, optionally substituted benzyl or optionally substituted fluorenyl;

$R^{47}$ represents H, $C_{1-6}$alkyl or $C_{2-6}$alkenyl;

$R^{48}$ represents phenyl($C_{1-4}$alkyl) optionally substituted in the phenyl ring by one or more groups selected from $C_{1-6}$alkyl, $C_{2-6}$alkenyl, $C_{2-6}$alkynyl, halo, cyano, nitro, trifluoromethyl, $SR^a$, $SOR^a$, $SO_2R^a$, $OR^a$, $NR^aR^b$, $NR^aCOR^b$, $NR^aCOOR^b$, $COOR^a$ and $CONR^aR^b$, where $R^a$ and $R^b$ are as defined for formula (1) above;

$Z^8$ represents O, S, $NR^{49}$ or $CR^{50}R^{51}$, where $R^{49}$ represents H, $C_{1-6}$alkyl, optionally substituted phenyl, optionally substituted phenyl($C_{1-4}$alkyl), $COR^{52}$, $COOR^{52}$ $CONR^{50}R^{51}$ where $R^{52}$ is optionally substituted phenyl, optionally substituted phenyl($C_{1-4}$alkyl) or $C_{1-6}$alkyl, and $R^{50}$ and $R^{51}$ each represents H, $C_{1-6}$alkyl, optionally substituted phenyl or optionally substituted phenyl($C_{1-4}$alkyl).

Suitable pharmaceutically acceptable salts of the compounds of formulae (1)-(8) include acid addition salts which may, for example, be formed by mixing a solution of the relevant compound with a solution of a pharmaceutically acceptable acid such as hydrochloric acid, sulphuric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds carry an acidic moiety, suitable pharmaceutically acceptable salts thereof may include metal salts such as alkali metal salts, e.g. sodium or potassium salts; and alkaline earth metal salts, e.g. calcium or magnesium salts.

In general, prodrugs of the compounds of formulae (1)-(8) will be functional derivatives of those compounds which are readily convertible in vivo into the required compound of formulae (1)-(8). Conventional procedures for the selection and preparation of suitable prodrug derivatives are described, for example, in "Design of Prodrugs", ed. H. Bundgaard, Elsevier, 1985.

Compounds of formula (1) above may be prepared by processes analogous to those described in European patent application no. 0 499 313.

The compounds of formula (2) wherein $X^2$ is OH may be prepared by reacting a compound of formula (9) with a compound of formula (10):

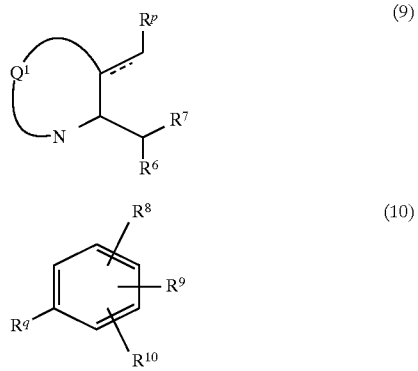

wherein $Q^1$ $R^6$ $R^7$, $R^8$, $R^9$ and $R^{10}$ are as defined in formula (2); $R^p$ represents CHO (intermediates (9B)); and $R^q$ is a metal, such as aluminium or lithium, or metal halide.

The group $R^q$ suitably represents a metal such as aluminium or, preferably, the residue of a Grignard agent such as MgBr. The reaction is preferably carried out in an inert organic solvent such as an ether such as diethyl ether, tetrahydrofuran or a mixture thereof.

The compounds of formula (2) wherein the double bond is present and $X^2$ is =O may be prepared by hydrolysing a compound of formula (11):

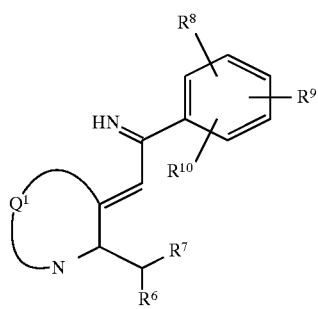

wherein $Q^1$, $R^6$, $R^7$, $R^8$, $R^9$ and $R^{10}$ are as defined in formula (2). The reaction may take place with dilute acid such as dilute mineral acid, for example, hydrochloric acid.

The compound of formula (11) need not be isolated but may be hydrolized in situ after being prepared from the corresponding compound of formula (9) wherein $R^p$ represents CN (9A) by reaction with the corresponding compound of formula (10) (wherein $R^q$ is preferably lithium) as described above in relation to preparing compounds of formula (2) wherein the double bond is present and $X^2$ is OH.

The compounds of formula (2) wherein the double bond is absent and $X^2$ is =O, or where $X^2$ is H or halo may be prepared from the corresponding compounds of formula (2) wherein $X^2$ is OH, by oxidation, reduction or halogenation, respectively, under conventional conditions.

The compounds of formula (9A) wherein the double bond is present may be prepared by reaction of a compound of formula (12) with a Wittig reagent:

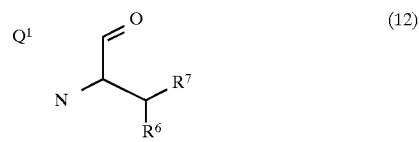

wherein $Q^1$, $R^6$ and $R^7$ are as defined in formula (2).

The compounds of formula (9A) wherein the double bond is absent may be prepared from the corresponding compounds of formula (9A) wherein the double is present, by reduction using conventional methods.

The intermediates of formula (9B) above wherein $R^p$ is CHO may be prepared by the procedures described in *J. Med. Chem.*, 1974, 17, 497, and *J. Med. Chem.*, 1975, 18, 587; or by methods analogous thereto.

Compounds of formula (12) are commercially available.

The compounds of formula (3) wherein $Z^3$ is O or S may be prepared by reaction of a compound of formula (13)

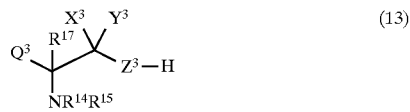

wherein $Q^3$, $R^{14}$, $R^{15}$, $R^{17}$, $X^3$ and $Y^3$ are defined as for formula (3) and $Z^3$ is O or S, with a compound of formula $R^{18}$Hal, where $R^{18}$ is as defined for formula (3) and Hal is halo, such as bromo, chloro or iodo, in the presence of a base.

The reaction is conveniently carried out in a suitable organic solvent, such as ether, for example, tetrahydrofuran, suitably at ambient temperature.

Suitable bases of use in the reaction include alkali or alkaline earth metal hydrides, for example, sodium hydride.

The compounds of formula (3) wherein $Z^3$ is a group $NR^{19}$ and $X^3$ and $Y^3$ together represent =O may be prepared from the compounds of formula (13) wherein $Z^3$ is O and $X^3$ and $Y^3$ together represent =O by reaction with a compound of formula $HNR^{19}R^{18}$ in the presence of a coupling agent, such as dicyclohexylcarbodiimide.

The reaction is suitably effected in an aprotic organic solvent, such as dichloromethane or dimethylformamide, or a mixture thereof.

The compounds of formula (3) wherein $Z^3$ is $NR^{19}$ and $X^3$ and $Y^3$ are H may be prepared from the corresponding compounds of formula (3) wherein $X^3$ and $Y^3$ together represent =O, by reduction.

Suitable reducing agents of use in the reaction include borane and metal hydrides, such as lithium aluminium hydride. The reaction is conveniently effected in a suitable organic solvent, such as an ether, for example, tetrahydrofuran.

Compounds of formula (13) wherein $Z^3$ is O and $X^3$ and $Y^3$ together represent a group =O may be prepared from intermediates of formula (14)

(14)

wherein $Q^3$ and $R^{17}$ are as above defined and Ph represents phenyl, by hydrolysis.

The reaction is conveniently effected by heating a solution of the compound of formula (4) in concentrated hydrochloric acid at reflux.

Compounds of formula (13) wherein $Z^3$ is S may be prepared from the corresponding compounds of formula (13) wherein $Z^3$ is O by treating the latter compound with Lawesson's reagent or phosphorus pentasulphide in a suitable solvent, e.g. pyridine, at ambient or elevated temperature, suitably at the reflux temperature of the chosen solvent.

Compounds of formula (13) wherein $X^3$ and $Y^3$ represent H may be prepared from the corresponding compounds of formula (13) wherein $X^3$ and $Y^3$ together represent =O, by reduction.

Intermediates of formula (14) may be prepared from compounds of formula (15)

(15)

wherein $R^{17}$ is as defined for formula (3), by reaction with a compound of formula $Q^3$-Hal, where $Q^3$ and Hal are as previously defined, in the presence of a base.

Suitable bases of use in the reaction include metal hydroxides, for example, sodium hydroxide. The reaction is conveniently effected in a mixture of water and a suitable organic solvent, such as a hydrocarbon, for example, toluene, in the presence of a phase transfer catalyst, such as benzyltrimethyl ammonium chloride.

Compounds of formula (15) are commercially available or may be prepared by procedures readily apparent to one skilled in the art.

Compounds of formula $Q^3$-Hal may be prepared according to the procedure described by E. J. Corey, *Tetrahedron Lett.*, 1972, 4339.

Compounds of formula (4) may be prepared analogously to compounds of formula (3), e.g. by reaction of an intermediate of formula (16):

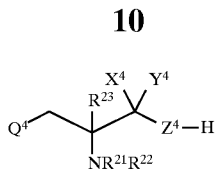
(16)

wherein $Q^4$, $R^{21}$, $R^{22}$, $R^{23}$, $X^4$ and $Y^4$ are as defined for formula (4) and $Z^4$ is O or S, with a compound of formula Hal—$CHR^{24}R^{25}$, where Hal, $R^{24}$ and $R^{25}$ are as previously defined, in the presence of a base.

Intermediates of formula (16) wherein $Z^4$ is O and $X^4$ and $Y^4$ together represent =O (16A) are commercially available or may be prepared by standard syntheses of amino acids. Such syntheses are well known to persons skilled in the art and are described, for example, in *Chemistry and Biochemistry of the Amino Acids*, ed. G. C. Barrett, Chapman and Hall, 1985.

Intermediates of formula (16) wherein $X^4$ and $Y^4$ are H and $Z^4$ is S may be prepared from the corresponding intermediates of formula (16) wherein $Z^4$ is O by treating the latter compound with Lawesson's reagent or phosphorus pentasulphide in a suitable solvent, e.g. pyridine, at ambient or elevated temperature, suitably at the reflux temperature of the chosen solvent.

Intermediates of formula (16) where $X^4$ and $Y^4$ are =O and $Z^4$ is S may be prepared from the corresponding compounds of formula (16A) by reaction with thionyl chloride, to give an acyl chloride, followed by treatment with hydrogen sulphide.

Intermediates of formula (16) wherein $X^4$ and $Y^4$ both represent H may be prepared from intermediates of formula (16) wherein $X^4$ and $Y^4$ together represent =O by reduction.

Compounds of formula (5) may be prepared analogously to compounds of formula (3), e.g. by reaction of an intermediate of formula (17):

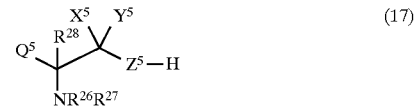
(17)

wherein $Q^5$, $R^{26}$, $R^{27}$, $R^{28}$, $X^5$ and $Y^5$ are as defined for formula (5) and $Z^5$ is O or S, with a compound of formula Hal—$CHR^{29}R^{30}$, in the presence of a base.

Compounds of formula (17) may be prepared analogously to compounds of formula (13).

Compounds of formula (6) may be prepared analogously to compounds of formula (3), e.g. by reaction of an intermediate of formula (18):

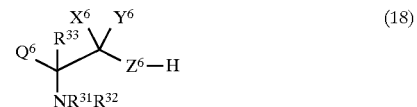
(18)

wherein $Q^6$, $R^{31}$, $R^{32}$, $R^{33}$, $X^6$ and $Y^6$ are as defined for formula (6) and $Z^6$ is O or S, with a compound of formula Hal—$CHR^{34}R^{35}$, in the presence of a base.

Compounds of formula (18) may be prepared analogously to compounds of formula (13).

Compounds of formula (7) may be prepared by methods analogous to those described in EP-A-0 499 313, e.g. by reaction of a compound of formula (19) with a compound of formula (20)

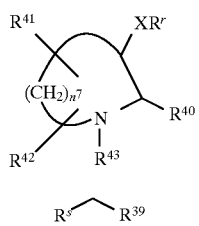

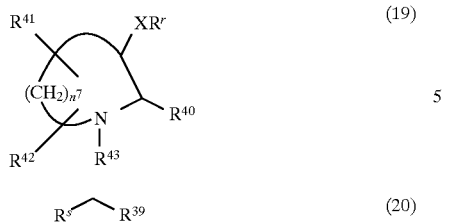

wherein $R^{39}$, $R^{40}$, $R^{41}$, $R_{42}$ and $n^7$ are as defined for formula (7), $R^{43}$ is as defined for formula (7) except that, when $R^{43}$ is H it is replaced by a suitable protecting group, such as $CO_2(C_{1-6}alkyl)$; and one of $R^r$ and $R^s$ represents a leaving group and the other of $R^r$ and $R^s$ represents $X^7H$, where $X^7$ is as defined for formula (7); in the presence of a base, followed by deprotection, if required.

The intermediates of formula (19) above wherein $R^r$ is SH may be prepared from the corresponding intermediates of formula (19) wherein $R^r$ represents OH by treating the latter compound with Lawesson's reagent or phosphorus pentasulphide in a suitable solvent, e.g. pyridine, at ambient or elevated temperatures, suitably at reflux temperature.

Intermediates of formula (19) above wherein $R^r$ is OH may be prepared from corresponding compounds of formula (21):

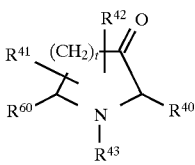

wherein $R^{40}$, $R^{41}$, $R^{42}$ and $R^{43}$ are as defined for formula (19) above, t is 1 or 2 and $R^{60}$ is an optional carbonyl group, by reduction. Suitable reducing agents will be readily apparent to one skilled in the art and include, for example, metallic hydrides, such as lithium aluminium hydride or, preferably, sodium borohydride.

Intermediates of formula (19) wherein $R^{30}$ is a leaving group may be prepared from compounds of formula (19) wherein $R^{30}$ is OH, for example, by reaction with a thionyl halide, a mesyl halide or a tosyl halide.

Compounds of formula (21) wherein t is 1, the carbonyl group $R^{60}$ is absent, and $R^{41}$ represents $CO_2(C_{1-6}alkyl)$, may be prepared by reaction of compounds of formula (22) with compounds of formula (23):

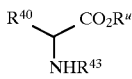

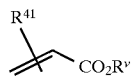

wherein $R^{40}$ is as above defined, $R''$ represents $C_{1-6}alkyl$ and $CO_2R^v$ is $R^{42}$; in the presence of a base.

Suitable bases include alkali metal hydrides, such as sodium hydride, and alkali metal alkoxides, such as sodium butoxide. The reaction is conveniently effected in a suitable organic solvent, such as a hydrocarbon, for example, benzene or toluene, or an ether, for example tetrahydrofuran.

Compounds of formula (21) wherein $R^{60}$ is absent and $R^{42}$ represents $CO_2(C_{1-6}alkyl)$ (21B), may be prepared by reaction of a compound of formula (22) with a compound of formula (23A)

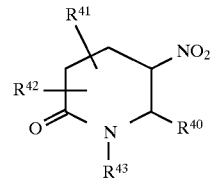

wherein t is 1 or 2, Hal and $CO_2R^v$ are as previously defined, in the presence of a base, as above described.

Compounds of formula (21) wherein $R^{41}$ is other than $CO_2(C_{1-6}alkyl)$ may be prepared from compounds of formula (21) wherein $R^{41}$ represents $CO_2(C_{1-6}alkyl)$ by decarboxylation using, for example, oxalic acid.

Compounds of formula (21) wherein t is 2 and the carbonyl group $R^{60}$ is present may be prepared from intermediates of formula (24):

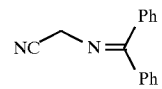

by ozonolysis, or by means of the Nef reaction. Suitable reagents and conditions are described in Organic Reactions, 38, 655.

Compounds of formula (21) wherein one or both of $R^{41}$ and $R^{42}$ represents halo, $C_{1-6}alkyl$, $CONR^{10}R^{11}$ or $CO_2R^{10}$ may be prepared from appropriately substituted analogues of the compounds of formulae (22), (23) and (23A), or by appropriate interconversion procedures which will be readily apparent to those skilled in the art.

Intermediates of formula (21) wherein $R''$ is $C_{1-6}alkyl$ (21A) may be prepared from the corresponding compounds of formula (21) wherein $R''$ is H (21B), by conventional methods.

Intermediates of formula (21B) may be prepared from the compound of formula (25):

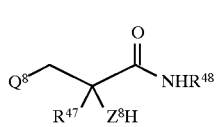

by reaction with a compound $R^{40}$-Hal, wherein $R^{40}$ and Hal are as previously defined in the presence of a base, followed by hydrolysis and suitable modification of the nitrogen substituent using conventional methods.

The compound of formula (25) is commercially available.

Intermediates of formula (24) are prepared as described in European Patent Application No. 0 436 334.

Compounds of formula $R^{40}$-Hal may be prepared according to the procedure described by E. J. Corey, Tetrahedron Lett., 1972, 4339.

The compounds of formula (8) wherein $Z^8$ is O, S or $NR^{49}$ may be prepared from intermediates of formula (26):

$$\text{(26)}$$

wherein $R^{47}$, $R^{48}$ and $Q^8$ are as defined for formula (8) above and $Z^8$ is O, S or $NR^{49}$, by reaction with phosgene or a "phosgene equivalent" such as carbonyl diimidazole, a dialkyl carbonate or an alkylchloroformate.

The reaction may be effected under basic conditions. Suitable bases include, for example, metal alkoxides such as sodium methoxide.

The compounds of formula (8) wherein $Z^8$ is $CR^{50}R^{51}$ may be prepared from intermediates of formula (27)

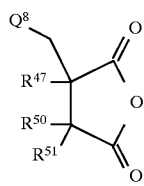

(27)

wherein $R^{47}$, $R^{50}$, $R^{51}$ and $Q^8$ are as defined for formula (8), by reaction with a compound of formula $R^{48}NH_2$ at elevated temperature.

Intermediates of formula (26) may be prepared from compounds of formula (28)

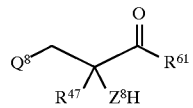

(28)

wherein
$R^{47}$ and $Q^8$ are as defined for formula (8), $Z^8$ is as defined for formula (26), and $R^{61}$ is an alkoxy, halo, hydroxy or $OCOR^{62}$ group where $R^{62}$ is alkyl, by reaction with a compound of formula $R^{48}NH_2$ under conventional conditions.

The group $Z^8H$ is suitably protected during the course of the amide bond forming reaction.

Compounds of formula (27) wherein $R^{47}$ is H may be prepared from the corresponding compounds of formula (29):

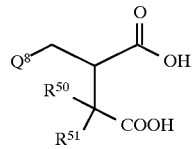

(29)

wherein $R^{50}$, $R^{51}$ and $Q^8$ are as defined for formula (8), by treatment with an anhydride, such as acetic anhydride.

Compounds of formula (29) may be prepared from compounds of formula (30A)

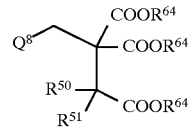

(30)

wherein $R^{50}$, $R^{51}$, and $Q^8$ are as defined for formula (I) and $R^{64}$ is H (30A), by decarboxylation.

Compounds of formula (30A) may be prepared from the corresponding compounds of formula (30) wherein $R^{47}$ is alkyl (30B) by treatment with a suitable base followed by protonation.

Compounds of formula (30B) may be prepared by reaction of compounds of formula $Q^8CH_2NR^{65}R^{66}$ wherein $R^{65}$ and $R^{66}$ each represent alkyl, with compounds of formula (31):

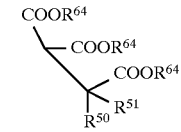

(31)

wherein $R^{50}$ and $R^{51}$ are as defined for formula (8) and $R^{64}$ is as defined for formula (30B), in the presence of catalytic sodium.

Compounds of formula (31) wherein $R^{50}$ and $R^{51}$ are H are commercially available. Compounds of formula (31) wherein $R^{50}$ and $R^{51}$ are not both H may be prepared by reaction of a compound of formula $CH_2(COOR^{64})_2$ with a compound of formula $R^{50}R^{51}C(COOR^{64})Hal$, where Hal is as previously defined in the presence of a base. Suitable bases include, for example, metal hydrides, such as sodium hydride.

Specific compounds of use in the present invention include:

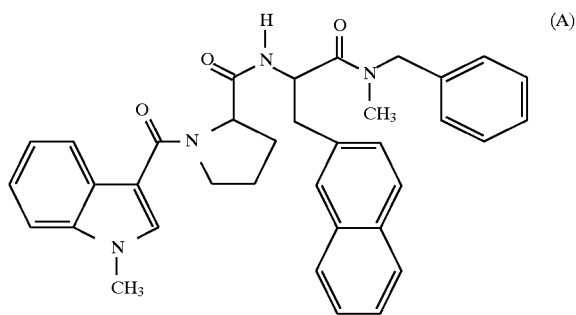

(A)

and

Cyclo(Gln—D—Trp—(N—Me)Phe—(R)Gly[ANC-2]Leu—Met$_2$). (B)

For use in accordance with the invention, NK1 receptor antagonists and their salts and prodrugs may be administered to humans, either alone or, preferably, in association with a pharmaceutically acceptable carrier in a pharmaceutical composition. Suitably these compositions are in unit dosage forms such as tablets, pills, capsules, powders, granules, sterile parenteral solutions or suspensions, or suppositories, for oral, parenteral or rectal administration. Preferably, the NK1 receptor antagonists will be formulated as a composition suitable for administration by inhalation or insufflation.

This invention provides such compositions.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from about 0.1 to about 500 mg of the active ingredient, for example 1 to 100 mg. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The compositions may be administered as needed, for example 1 to 5 times daily, more usually 2 or 3 times daily.

The liquid forms in which the compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. A particularly apt solid insufflatable powder carrier is lactose. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

This invention includes compositions adapted to administration by insufflation or inhalation. Most aptly such compositions are contained within a device to aid their administration. Most aptly such devices are a nebulizer or insufflation device.

What is claimed is:

1. A method of treating cystic fibrosis which comprises administering to a patient in need thereof an effective amount of a tachykinin receptor antagonist which is a NK1 receptor antagonist.

2. A method according to claim 1 wherein the receptor NK1 receptor antagonist is administered orally.

3. A method according to claim 1 wherein the NK1 receptor antagonist is administered by insufflation or inhalation.

4. A method according to claim 1 wherein said tachykinin antagonist is of the formula:

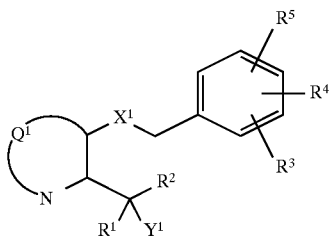

(1)

wherein $Q^1$ is a quinuclidine ring system;

$X^1$ represents O or S;

$Y^1$ represents H or hydroxy;

$R^1$ represents phenyl or thienyl, either of which groups may be optionally substituted by halo, trifluoromethyl or $C_{1-3}$ alkoxy, or $C_{5-7}$ cycloalkyl;

$R^2$ represents benzyl which may be substituted in the benzyl ring by halo, trifluoromethyl or $C_{1-3}$alkoxy, or $C_{5-7}$ cycloalkyl; and $R^3$, $R^4$ and $R^5$ independently represent H, $C_{1-6}$ alkyl, $C_{2-6}$ alkenyl, $C_{2-6}$ alkynyl, halo, cyano, nitro, trifluoromethyl, trimethylsilyl, —$OR^a$, $SCH_3$, $SOCH_3$, $SO_2CH_3$, —$NR^aR^b$, —$NR^aCOR^b$, —$NR^aCO_2R^b$, —$CO_2R^a$ or —$CONR^aR^b$; and $R^a$ and $R^b$ independently represent H, $C_{1-6}$ alkyl, phenyl or trifluoromethyl.

5. A method according to claim 1 wherein said tachykinin antagonist is of the formula:

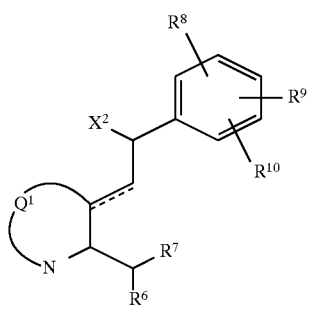

(2)

wherein $Q^1$ is a quinuclidine ring system;

the dotted line represents an optional double bond;

$X^2$ represents H, —OH, =O or halo;

$R^6$ represents H, phenyl or thienyl, which phenyl or thienyl groups may be optionally substituted by halo or trifluoromethyl;

$R^7$ represents phenyl, thienyl or benzyl, any of which groups may be optionally substituted by halo or trifluoromethyl; and $R^8$, $R^9$ and $R^{10}$ independently represent H, $C_{1-6}$ alkyl, $C_{2-6}$ alkenyl, $C_{2-6}$ alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$ or —$CONR^aR^b$; where $R^a$ and $R^b$ independently represent H, $C_{1-6}$alkyl, phenyl or trifluoromethyl.

6. A method according to claim 1 wherein said tachykinin antagonist is of the formula:

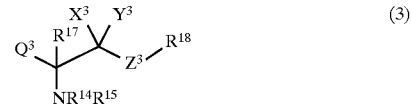

(3)

wherein $Q^3$ represents $R^{11}CR^{12}R^{13}$ or $CH_2R^{11}CR^{12}R^{13}$ where $R^{11}$ is H or hydroxy and $R^{12}$ and $R^{13}$ each independently represent phenyl, benzyl, $C_{5-7}$cycloalkyl or ($C_{5-7}$cycloalkyl)methyl;

$R^{14}$ and $R^{15}$ independently represent H; $C_{1-6}$ alkyl optionally substituted by hydroxy, cyano, $COR^c$, $COOR^c$, $CONR^cR^d$, $COC_{1-6}$alkyl$NR^cR^d$, $CONR^{16}C_{1-6}$alkyl$OR^c$, $CONR^{16}C_{1-6}$alkyl$CONR^cR^d$ or $NR^cR^d$, where $R^c$ and $R^d$ each independently represent H, $C_{1-6}$alkyl, phenyl, optionally substituted in the phenyl ring by one or more of $C_{1-6}$alkyl, $C_{1-6}$alkoxy, halo and trifluoromethyl, or $R^c$ and $R^d$ together form a chain $(CH_2)_p$, optionally substituted by oxo, where p is 4 or 5 and where one methylene group may optionally be replaced by an oxygen atom or a group $NR^x$, where $R^x$ is H or $C_{1-6}$alkyl, and $R^{16}$ represents H, $C_{1-6}$alkyl, phenyl (optionally substituted by one or more of $C_{1-6}$alkyl, $C_{1-6}$alkoxy, halo and trifluoromethyl) or phenyl ($C_{1-4}$alkyl), optionally substituted in the phenyl ring by one or more of $C_{1-6}$alkyl, $C_{1-6}$alkoxy, halo and trifluoromethyl; phenyl ($C_{1-4}$alkyl), optionally substituted by one or more of $C_{1-6}$alkyl, $C_{1-6}$alkoxy, halo and trifluoromethyl; phenyl ($C_{1-4}$alkyl), optionally substituted by one or more of $C_{1-6}$alkyl, $C_{1-6}$alkoxy, halo and trifluoromethyl in the phenyl ring); $C_{2-6}$alkenyl; $C_{2-6}$alkynyl; $COR^c$; $COOR^c$; $COC_{1-6}$alkylhalo; $COC_{1-6}$alkyl$NR^cR^d$; $CONR^{16}C_{1-6}$alkyl$CONR^cR^d$; $CONR^cR^d$; or $SO_2R^c$;(where $R^c$, $R^d$ and $R^{16}$ are as previously defined, or $R^{14}$ and $R^{15}$ together form a chain $(CH_2)_q$ optionally substituted by oxo where q is 4 or 5 and where one methylene group may optionally be replaced by an oxygen atom or a group $NR^x$, where $R^x$ is H or $C_{1-6}$alkyl;

$R^{17}$ represents H, $C_{1-6}$alkyl or $C_{2-6}$alkenyl;

$R^{18}$ represents $C_{1-3}$alkyl substituted by a phenyl group which may itself optionally be substituted by one or more of $C_{1-6}$alkyl, $C_{2-6}$alkenyl, $C_{2-6}$alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ and $CONR^aR^b$, where $R^aR^b$ independently represent H, $C_{1-6}$alkyl, phenyl or trifluoromethyl;

$X^3$ and $Y^3$ each represent H, or $X^3$ and $Y^3$ together represent a group =O; and $Z^3$ represents O, S, or $NR^{19}$, where $R^{19}$ represents H or $C_{1-6}$alkyl.

7. A method according to claim 1 wherein said tachykinin antagonist is of the formula:

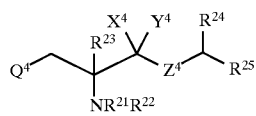

wherein
  $Q^4$ represents phenyl, naphthyl, indolyl, benzthiophenyl, benzofuranyl, benzyl or indazolyl;
  $Z^4$ represents O, S or $NR^{20}$, where $R^{20}$ is H or $C_{1-6}$alkyl;
  $X^4$ and $Y^4$ each represent H or $X^4$ and $Y^4$ together form a group =O;
  $R^{21}$ and $R^{22}$ each independently represent H; $C_{1-6}$alkyl, optionally substituted by hydroxy, cyano, CORg, $CO_2$Rg, $CONRgR^h$, or $NRgR^h$, where Rg and $R^h$ each independently represent H, $C_{1-12}$alkyl or phenyl optionally substituted by one or more of $C_{1-6}$alkyl, $C_{1-6}$alkoxy, halo or trifluoromethyl) phenyl ($C_{1-4}$alkyl), optionally substituted by one or more of $C_{1-6}$alkyl, $C_{1-6}$alkoxy, halo or trifluoromethyl; phenyl ($C_{1-4}$alkyl), optionally substituted in the phenyl ring by one or more of $C_{1-6}$alkyl, $C_{1-6}$alkoxy, halo and trifluoromethyl) CORg; $CO_2$Rg; $CONRgR^h$; $CONRgCOOR^h$; or $SO_2$Rg, where Rg and $R^h$ are as above defined;
  $R^{23}$ represents H or $C_{1-6}$alkyl; and
  $R^{24}$ represents H, $C_{1-6}$alkyl or phenyl, optionally substituted by 1, 2, or 3 groups selected from $C_{1-6}$alkyl, $C_{2-6}$alkenyl, $C_{2-6}$alkynyl, halo cyano, nitro, trifluoromethyl, trimethylsilyl, $OR^a$, $SR^a$, $SOR^a$, $NR^aR^b$, $NR^aCOR^b$, $CO_2R^a$ and $CONR^aR^b$, where $R^a$ and $R^b$ independently represent H, $C_{1-6}$alkyl, phenyl or trifluoromethyl; and
  $R^{25}$ represents phenyl, optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ and $CONR^aR^b$, where $R^a$ and $R^b$ independently are as above defined.

8. A method according to claim 1 wherein said tachykinin antagonist is of the formula:

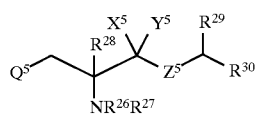

wherein
  $Q^5$ represents phenyl or napthyl;
  $X^5$ and $Y^5$ each represent H, $C_{1-6}$alkyl, $C_{2-6}$alkenyl or $X^5$ and $Y^5$ together form a group =O;
  $Z^5$ represents O or S;
  $R^{26}$ represents H; $C_{1-6}$alkyl, optionally substituted by hydroxy, cyano, CORj, COORj, $CONRjR^k$, $COC_{1-4}$alkylNRjR$^k$, $CONRjC_{1-4}$alkylCONjR$^k$ or NRjR$^k$, where $R^j$ and $R^k$ each independently represent H, $C_{1-6}$ alkyl, phenyl optionally substituted by one or more of $C_{1-6}$alkyl, $C_{1-6}$alkoxy, halo or trifluoromethyl or phenyl ($C_{1-4}$alkyl) optionally substituted in the phenyl ring by one or more of $C_{1-6}$ alkyl, $C_{1-6}$ alkoxy, halo or trifluoromethyl); phenyl ($C_{1-4}$ alkyl), optionally substituted in the phenyl ring by one or more of $C_{1-6}$ alkyl, $C_{1-6}$ alkoxy, halo or trifluoromethyl; $C_{2-6}$ alkylene; CORj, COORj; CONHRj; $COC_{1-6}$alkylhalo; $COC_{1-6}$alkylNRjR$^k$; or $CONRjC_{1-6}$alkylCONRjR$^k$, where $R^j$ and $R^k$ are as previously defined;
  $R^{27}$ represents $C_{1-6}$ alkyl substituted by hydroxy, cyano, CORj, COORj, CONRjR$^k$, $COC_{1-4}$alkylNRjR$^k$, $CONRjC_{1-4}$alkylCONRjR$^k$ or NRjR$^k$, where $R^j$ and $R^k$ are as above defined) phenyl ($C_{1-4}$ alkyl), optionally substituted by one or more of $C_{1-6}$ alkyl, $C_{1-6}$ alkoxy, halo and trifluoromethyl in the phenyl ring); $C_{2-6}$ alkylene; CORj; COORj; CONHRj; $COC_{1-6}$alkylhalo; $COC_{1-6}$alkylNRjR$^k$; or $CONRjC_{1-6}$alkylCONRjR$^k$, where $R^j$ and $R^k$ are as previously defined;
  or $R^{26}$ and $R^{27}$ together form a chain $(CH_2)_p$ optionally substituted by oxo; where p is 4 or 5 and where one methylene group may optionally be replaced by an oxygen atom or a group $NR^x$, where $R^x$ is H or $C_{1-6}$ alkyl;
  $R^{28}$ represents H or C1-6alkyl;
  $R^{29}$ represents H, $C_{1-6}$ alkyl or phenyl, optionally substituted by one or more of $C_{1-6}$ alkyl, $C_{2-6}$ alkenyl, $C_{2-6}$ alkynyl, halo, cyano, nitro, trifluoromethyl, trimethylsilyl, $SR^a$, $SOR^a$, $SO_2R^a$, $OR^a$, $NR^aR^d$, $NR^aCOR^b$, $NR^aCOOR^b$, $COOR^a$ or $CONR^aR^b$, where $R^a$ and $R^b$ independently represent H, $C_{1-6}$alkyl, phenyl or trifluoromethyl; and
  $R^{30}$ represents $(CH_2)_q$phenyl, wherein q is 0, 1, 2 or 3, which may optionally be substituted in the phenyl ring by one or more of $C_{1-6}$ alkyl, $C_{2-6}$ alkenyl, $C_{2-6}$ alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ are as above defined.

9. A method according to claim 1 wherein said tachykinin antagonist is of the formula:

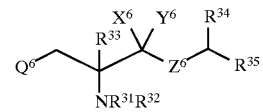

wherein
  $Q^6$ represents a group

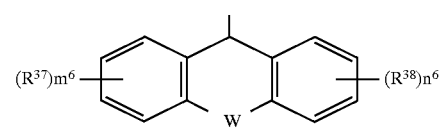

where W represents a bond, O, S, —$CH_2CH_2$—, —CH=CH—, or a group $NR^{36}$, where $R^{36}$ is H or $C_{1-6}$alkyl;
  $X^6$ and $Y^6$ each represent H or $X^6$ and $Y^6$ together form a group =O;
  $Z^6$ represents O, S or $NR^{38}$, where $R^{38}$ represents H or $C_{1-6}$alkyl;
  $R^{31}$ and $R^{32}$ independently represent H; $C_{1-6}$ alkyl optionally substituted by hydroxy, cyano, $COR^e$, $COOR^e$, $CONR^eR^f$, $COC_{1-4}$alkyl$NR^eR^f$, $CONR^eC_{1-4}$alkyl-$CONR^eR^f$ or $NR^eR^f$, where $R^e$ and $R^f$ each independently represent H, $C_{1-6}$ alkyl, phenyl, optionally substituted by one or more of $C_{1-6}$ alkyl, $C_{1-6}$alkoxy, halo and trifluoromethyl, or phenyl ($C_{1-4}$alkyl), optionally substituted in the phenyl ring by one or more of $C_{1-6}$ alkyl, $C_{1-6}$ alkoxy, halo and trifluoromethyl; phenyl ($C_{1-4}$ alkyl), optionally substituted by one or more of $C_{1-6}$ alkyl, $C_{1-6}$ alkoxy, halo and trifluoromethyl in the phenyl ring; $C_{2-6}$ alkylene; $COC_{1-6}$alkylhalo; $COR^e$; $COOR^e$; $CONHR^e$; $COC_{1-4}$alkyl$NR^eR^f$; or $CONR^eC_{1-4}$alkyl$CONR^eR^f$; where $R^e$ and $R^f$ are as previously defined; or $R^{31}$ and $R^{32}$ together form a chain $(CH_2)_p$ where p is 4 or 5 and where one non-terminal methylene group may optionally be replaced by an oxygen atom or a group $NR^x$, where $R^x$ is H or $C_{1-6}$ alkyl;

$R^{33}$ represents H or $C_{1-6}$alkyl;

$R^{34}$ represents H, $C_{1-6}$ alkyl or phenyl, optionally substituted by one or more of $C_{1-6}$ alkyl, $C_{2-6}$ alkenyl, $C_{2-6}$ alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ independently represent H, $C_{1-6}$alkyl, phenyl or trifluoromethyl;

$R^{35}$ represents $(CH_2)_q$phenyl, wherein q is 0, 1, 2 or 3 which may optionally be substituted in the phenyl ring by one or more of $C_{1-6}$ alkyl, $C_{2-6}$ alkenyl, $C_{2-6}$ alkynyl, halo, cyano, nitro, trifluoromethyl, trimethylsily, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ are as above defined;

each $R^{37}$ and $R^{38}$ independently represents $C_{1-6}$ alkyl, $C_{2-6}$ alkenyl, $C_{2-6}$ alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ are as above defined; and $m^6$ and $n^6$ independently represent 0, 1, 2, 3 or 4.

10. A method according to claim 1 wherein said tachykinin antagonist is of the formula:

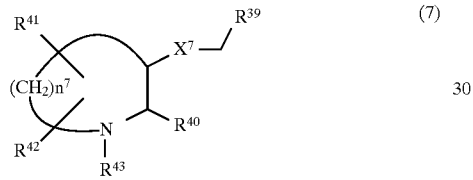 (7)

wherein $n^7$ is 1, 2 or 3 and any carbon atom of $(CH_2)_n^7$ may be substituted by $R^{41}$ and/or $R^{42}$;

$X^7$ represents O or S;

$R^{39}$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, $-OR^a$, $SR^a$, $SOR^a$, $SO_2R^a$, $-NR^aR^b$, $-NR^aCOR^b$, $-NR^aCO_2R^b$, $-CO_2R^a$ or $-CONR^aR^b$;

$R^{40}$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;

$R^{41}$ and $R^{42}$ each independently represent H, halo, $CH_2OR^{44}$, $C_{1-6}$alkyl, oxo, $CO_2R^{45}$ or $CONR^{45}R^{46}$;

$R^{43}$ represents H, $COR^{44}$, $CO_2R^{45}$, $COCONR^{45}R^{46}$, $COCO_2R^{45}$ or $C_{1-6}$alkyl optionally substituted by a group selected from $CO_2R^{45}$, $CONR^{45}R^{46}$, hydroxy, cyano, $COR^{44}$, $NR^{45}R^{46}$, $C(NOH)NR^{45}R^{46}$, CONHphenyl ($C_{1-4}$alkyl), $COCO_2R^{45}$, $COCONR^{45}R^{46}$ and phenyl optionally substituted by one or more substituents selected from $C_{1-6}$alkyl, $C_{1-6}$alkoxy, halo and trifluoromethyl;

$R^a$ and $R^b$ independently represent H, $C_{1-6}$alkyl, phenyl or trifluoromethyl;

$R^{44}$ represents H, $C_{1-6}$alkyl or phenyl; and $R^{45}$ and $R^{46}$ each independently represent H or $C_{1-6}$alkyl.

11. A method according to claim 1 wherein said tachykinin receptor antagonist is of the formula:

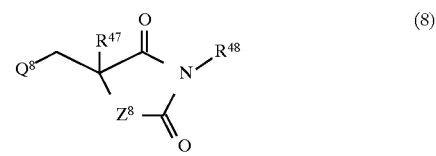 (8)

wherein $Q^8$ represents a phenyl group substituted by one or more halo, naphthyl, indolyl, benzthiophenyl, benzofuranyl, benzyl or fluorenyl;

$R^{47}$ represents H, $C_{1-6}$alkyl or $C_{2-6}$alkenyl;

$R^{48}$ represents phenyl ($C_{1-4}$alkyl) optionally substituted in the phenyl ring by one or more groups selected from $C_{1-6}$ alkyl, $C_{2-6}$ alkenyl, $C_{2-6}$ alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ independently represent H, $C_{1-6}$alkyl, phenyl or trifluoromethyl;

$Z^8$ represents O, S, $NR^{49}$ or $CR^{50}R^{51}$, where $R^{49}$ represents H, $C_{1-6}$alkyl, optionally substituted phenyl, optionally substituted phenyl ($C_{1-4}$alkyl), $COR^{52}$, $COOR^{52}$, $CONR^{50}R^{51}$ where $R^{52}$ is optionally substituted phenyl, optionally substituted phenyl ($C_{1-4}$alkyl) or $C_{1-6}$alkyl, and $R^{50}$ and $R^{51}$ each represents H, $C_{1-6}$alkyl, optionally substituted phenyl or optionally substituted phenyl ($C_{1-4}$alkyl).

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Arg  Pro  Lys  Pro  Gln  Glu  Phe  Phe  Gly  Leu  Met
1                   5                        10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
His  Lys  Thr  Asp  Ser  Phe  Val  Gly  Leu  Met
1                   5                   10
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Asp  Met  His  Asp  Phe  Phe  Val  Gly  Leu  Met
1                   5                        10
```